United States Patent
Tkaczyk et al.

(10) Patent No.: US 9,237,872 B2
(45) Date of Patent: Jan. 19, 2016

(54) X-RAY SOURCE WITH MOVING ANODE OR CATHODE

(71) Applicant: General Electric Company, Schenectady, NY (US)

(72) Inventors: John Eric Tkaczyk, Niskayuna, NY (US); Remy Andre Klausz, BUC (FR); Scott Stephen Zelakiewicz, Niskayuna, NY (US); Vasile Bogdan Neculaes, Niskayuna, NY (US); Xi Zhang, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 233 days.

(21) Appl. No.: 13/744,662

(22) Filed: Jan. 18, 2013

(65) Prior Publication Data
US 2014/0205073 A1   Jul. 24, 2014

(51) Int. Cl.
| | | |
|---|---|---|
| *H01J 35/00* | (2006.01) | |
| *A61B 6/02* | (2006.01) | |
| *A61B 6/00* | (2006.01) | |
| *H01J 35/26* | (2006.01) | |
| *H01J 35/28* | (2006.01) | |
| *H01J 35/10* | (2006.01) | |

(52) U.S. Cl.
CPC .............. *A61B 6/025* (2013.01); *A61B 6/4021* (2013.01); *A61B 6/502* (2013.01); *H01J 35/26* (2013.01); *H01J 35/28* (2013.01); *A61B 6/542* (2013.01); *H01J 35/10* (2013.01)

(58) Field of Classification Search
CPC ....................................................... H01J 35/28
USPC ......... 378/4, 9, 10, 19, 23, 25, 26, 27, 37, 55, 378/69, 74, 92, 96, 98.6, 98.9, 101, 121, 378/134, 135, 136, 144, 146, 148, 157, 196, 378/197, 201, 208
See application file for complete search history.

(56) References Cited

U.S. PATENT DOCUMENTS

| | | | |
|---|---|---|---|
| 4,187,442 A | | 2/1980 | Hueschen et al. |
| 4,281,269 A | * | 7/1981 | Ledley ..................... 378/126 |
| 5,305,363 A | | 4/1994 | Burke et al. |
| 6,125,167 A | | 9/2000 | Morgan |
| 6,553,096 B1 | | 4/2003 | Zhou et al. |
| 7,065,179 B2 | | 6/2006 | Block et al. |
| 7,305,063 B2 | * | 12/2007 | Heuscher ..................... 378/12 |
| 7,751,530 B2 | | 7/2010 | Sridhar et al. |
| 8,130,897 B2 | * | 3/2012 | Popescu et al. ................ 378/4 |
| 8,259,905 B2 | * | 9/2012 | Al-Sadah et al. ............. 378/126 |
| 2010/0020936 A1 | * | 1/2010 | Fritzler et al. ............... 378/136 |
| 2011/0051895 A1 | | 3/2011 | Vogtmeier et al. |
| 2011/0188624 A1 | | 8/2011 | Ren et al. |

OTHER PUBLICATIONS

Jimmy et al, "CT Physics and Instrumentation—Mechanical Design", Veterinary Computed Tomography, First Edition.

* cited by examiner

*Primary Examiner* — Hoon Song
(74) *Attorney, Agent, or Firm* — Robert M. McCarthy

(57) ABSTRACT

An X-ray source comprising a cathode element adapted to generate a stream of electrons. The X-ray source includes an anode element adapted to present a focal spot position for the stream of electrons. A vacuum chamber contains the cathode element and anode element. The anode element and/or the cathode element can be moveable with respect to the other in coordination with the generation of the stream of electrons.

16 Claims, 9 Drawing Sheets

X-RAY SOURCE WITH MOVING ANODE OR CATHODE

BACKGROUND

The present invention is generally related to an X-ray tube assembly and more particularly to an X-ray tube assembly in which anode or cathode elements are moveable with respect to each other.

Radiographic imaging systems, such as X-ray and computed tomography (CT) have been employed for observing interior aspects of an object. Typically, the imaging systems include an X-ray source that is configured to emit X-rays toward an object of interest, such as a patient. A detecting device, such as an array of radiation detectors, is positioned on the other side of the object and is configured to detect the X-rays transmitted through the object of interest.

X-ray or radiographic imaging is the basis of a number of diagnostic imaging systems. Computed tomography (CT) is one example of such a system that is predicated upon the acquisition of data using the principles of radiography. By mapping the incomplete penetration of X-rays through an object from multiple different angles, CT image systems generate volumetric representations of the object. Dedicated Breast Tomography (DBT) operates under similar principles to CT, but, whereas CT generally acquires data a full 360 degree range of angles about the imaged object, DBT will acquire only a limited range of angles such as 30 to 120 degrees and with a system geometry optimized to breast imaging, Typically, in CT and DBT imaging systems, a single X-ray source emits a single fan-shaped or cone-shaped beam toward a subject or object, such as a patient or a piece of luggage. The imaging angle is defined relative to the fixed imaged object by a line that joins the focal spot location in the tube to the detector center. In a moving source configuration, the angle is changed by moving the source relative to the fixed subject and collecting data at times. In a distributed source configuration, multiple focal spot locations are provided in the system and are energized in a sequence so as to provide data at different imaging angles. The beam, after being attenuated by the subject, impinges upon an array of radiation elements. One embodiment of this array could be a pixel array within a radiographic detector or multiple pixels spread over multiple discreet detectors. The intensity of the attenuated beam radiation received at the detector array is typically dependent upon the attenuation of the X-ray beam by the subject. Each detector element of the detector array produces a separate electrical signal indicative of the attenuated beam received by each detector element. The electrical signals are transmitted to a data processing system for analysis which ultimately produces an image.

Generally, for CT the X-ray source and the detector array are rotated about an axis within an imaging plane and around the subject. For DBT, the X-ray source is moved relative to the subject and the detector may or may not move. X-ray sources typically include X-ray tubes, which emit the X-ray beam at a focal point. X-ray detectors typically include a collimator for collimating X-ray beams received at the detector, a scintillator for converting X-rays to light energy adjacent the collimator, and photodiodes for receiving the light energy from the adjacent scintillator and producing electrical signals therefrom. Alternately, a photoconductor layer can serve a combined function of the scintillator and photodiodes by directly absorbing X-rays and converting directly to electrical signals.

In an indirect detector type, the scintillator converts X-rays to light energy. The scintillator discharges light energy to a photodiode adjacent thereto. Each photodiode detects the light energy and generates a corresponding electrical signal. In a direct detector type, the photoconductor converts X-rays to electric charge in proportion to the energy and delivers that charge under the influence of a high voltage to electrical contacts. The outputs of the photodiodes or photoconductor are then transmitted to the data processing system for image reconstruction. Other types of radiation detectors exist such as those that convert X-rays directly to electrical signals without the use of a scintillator or photodiode.

CT systems, as well as X-ray systems, typically utilize a rotating anode during the data acquisition process. Rotating the anode presents a moving electrode track at the spot which generates the X-ray fan beam, and thereby spreads the thermal load on an enlarged surface area of the anode. That is, the anode typically includes a single target electrode that is mounted or integrated with an anode disc. The anode disc may be rotated by an induction motor during data acquisition. Rotation is initiated before the start of a mechanical scan of the source. The rotation rate is maintained at a constant rate throughout the source trajectory and not coordinated specifically with the acquisitions of data at multiple locations. Since the electrons striking the anode deposit most of their energy as heat, with a small fraction emitted as X-rays, producing X-rays in quantities sufficient for acceptable image quality generates a large amount of heat. It can be the case that the heat is generated sufficiently rapidly and in a small focal area on the anode electrode surface as to raise the temperature close to the melting temperature of the electrode material or creating destructive thermal strain and shock. The consequences of such thermal overloading can be melting or cracking on the anode surface. A number of techniques have been developed to accommodate the thermal load placed on the anode during the X-ray generate process.

For example, advancements in the detection of X-ray attenuation has allowed for a reduction in X-ray dose necessary for delivering images with sufficient quality. X-ray dose delivered to the patient and tube current are directly related and, as such, a reduction in tube current results in a reduction in X-ray dosage. Similarly, a drop in tube current, i.e. reduction in the number of striking electrons on the anode target, reduces the thermal load placed on the anode target during data acquisition. Simply, less power is needed to generate the X-ray necessary for data acquisition. However, counteracting the advances in detection equipment is the need to decrease scan time or increase throughput (e.g. patients per hour) that call for increased X-ray power. X-rays are generated at a focal local on the anode electrode as a result of electrons emitted from a cathode striking a target electrode mounted to or integrated with the anode disc. A control circuit sets the number of electrons emitted from the cathode and the voltage potential placed across the cathode and anode in order meet the imaging requirements and to protect the tube from overheating. Total heat load on the anode that is proportional to the emitted current and the voltage potential placed across the cathode and anode. Optimal patient safety conditions can call for higher tube voltage or pre-patient attenuation filters that drive higher X-ray power requirements that challenge the thermal condition of the anode. In spite of advances in detection equipment, a minimum number of electrons must be generated for meaningful data acquisition under the constraints of minimum patient dose or increased throughput. As a result, a mere reduction in tube current is insufficient to address the thermal load on the anode resulting from X-ray generation.

Another approach is predicated upon the spreading of the generated heat across the surface and mass of the anode disc.

By rotating the anode disc as electrons are striking the target electrode, the heat generated therefrom may be spread across a track of the anode disc rather than at a single focal location on the target electrode surface. This rotation of the anode disc effectively reduces the thermal load placed at any single location on target electrode. As a result, tube current may be increased without thermal overloading of the anode. Generally, the faster the anode disc is rotated the higher the tube current that may be used.

Increasing the tube current and effectively the power levels of the X-ray tube assembly is particularly desirable for short duration high power reconstruction protocols. With these protocols, the gantry is caused to rotate at significantly fast rotational speeds. Through increased rotational gantry speed, the overall exam time may be decreased. Decreasing the overall exam or scan time improves patient throughput and reduces patient discomfort which reduces patient-induced motion artifacts in the reconstructed image. To support faster gantry speeds, the X-ray tube must output sufficiently more instantaneous power which is required for short duration protocols.

To provide the requisite instantaneous power needed for short duration protocols, the X-ray tube must output more power without exceeding the thermal load of the target electrode. As mentioned above, rotating the anode disc during X-ray generation reduces the thermal load on the electrode target.

SUMMARY

An X-ray source comprising a cathode element adapted to generate a stream of electrons. The X-ray source includes an anode element adapted to present a focal spot position for the stream of electrons. A vacuum chamber contains the cathode element and anode element. The anode element and/or the cathode element can be moveable with respect to the other in coordination with the generation of the stream of electrons.

DETAILED DESCRIPTION

Figure 1:
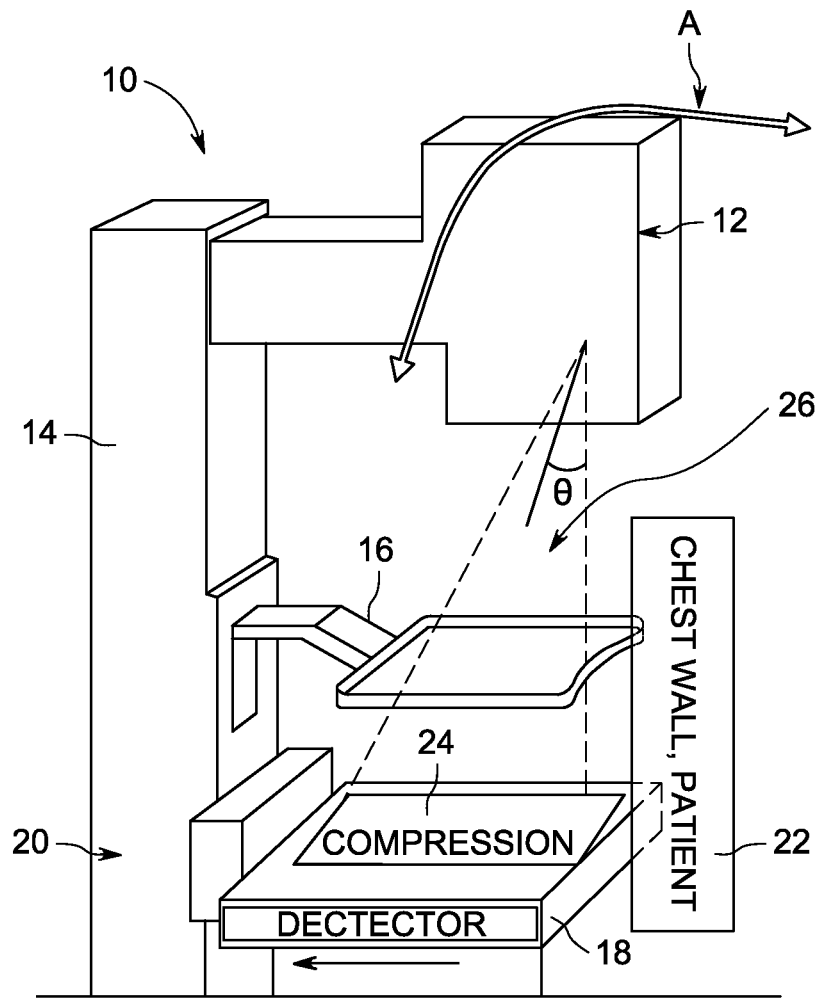
FIG. 1 is a perspective view of an X-ray tomosynthesis mammography imaging system according to one embodiment of the present disclosure.

Referring to FIG. 1, an embodiment of an X-ray dedicated breast tomography imaging system 10 is shown including an X-ray source housing 12 mounted an on upper part of movable arm 14. Housing structure 20 supports compression paddle 16 and detector 18. In an exemplary embodiment, patient 22 places breast 24 under compression paddle 16 to be imaged by system 10. To provide further images and create three-dimension images, movable arm 14 is repositionable along arc A. X-ray illumination area 26 is directed downward toward detector 18 with angle θ defining the width of X-ray illumination area 26 generated by X-ray source 12.

While exemplary embodiments of the X-ray tube modules are described relative to a dedicated breast tomography imaging system, those skilled in the art will recognize that the detector modules can be utilized in other systems for detecting radiation and rendering projection and volumetric representations of the imaged objects. For example, in some embodiments, the X-ray tube modules can be used in computed tomography (CT) scanners, fluoroscopy systems used in angiography and cardiac medical imaging, radiographic medical imaging, radiographic tomography imaging, distributed source X-ray scanners, and X-ray scanners for luggage or in gamma ray detectors.

Figure 2:
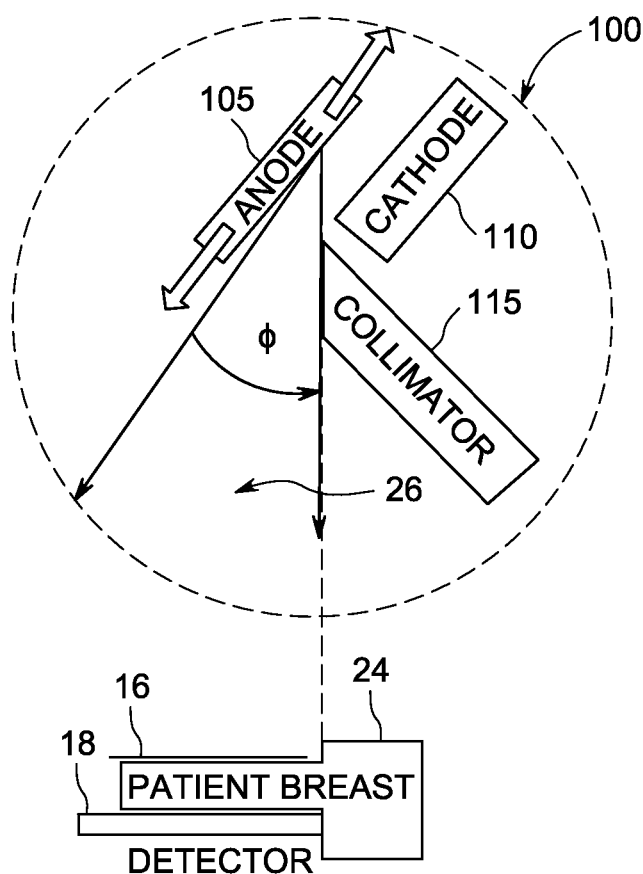
FIG. 2 is a side view of an X-ray tube according to an exemplary embodiment of the present disclosure, showing a moving anode and fixed cathode, collimator and detector.

Referring now to FIG. 2, a side schematic view of an exemplary embodiment of an X-ray tube 100 is shown. X-ray assembly tube 100 forms X-ray projection source 12 of FIG. 1. Cathode 110 generates a stream of electrons that strike the face of anode 105. In one exemplary embodiment, anode 105 is a flat structure which moves parallel with respect to cathode 110 to present a constant focal spot position for the stream of electrons. The translation of the anode 105 in the most general sense can be motion that is linear or rotational, continuous, stepped, or oscillatory, and in one or more direction simultaneously. A translation of the anode serves to spread heat across a larger surface area and limits the maximum temperature. A control system is operationally connected to the energizing circuit of the cathode 110 and the translation mechanism of the anode 105 in order to coordinate the electron emission from the cathode to the relative motion of the anode. The coordination is engineered to support the thermal load at the anode due to the level of emission current. A vacuum chamber (not shown) contains cathode 110 and anode 105. Angle φ corresponds to an anode target angle which defines X-ray illumination area 26. Optionally, collimator 115 is utilized to further shape X-ray illumination area 26.

Figure 3:
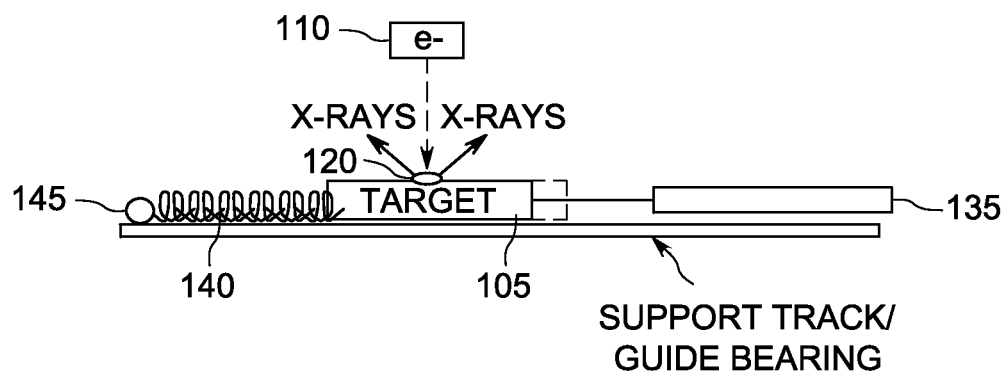
FIG. 3 is a schematic side view of the anode of FIG. 2, showing a linear actuator and spring positioning system connected to the anode.
Figure 4:
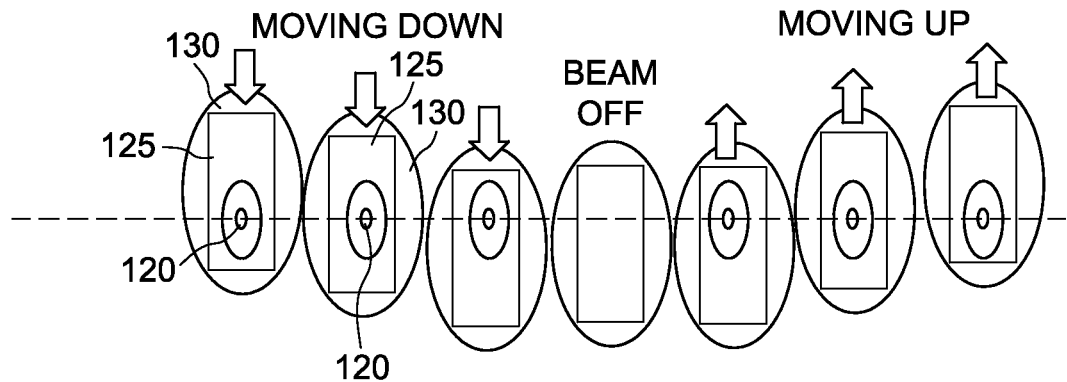
FIG. 4 is a front plan view of the anode of FIG. 2, showing vertical movement of the focal spot position over time.
Figure 5:
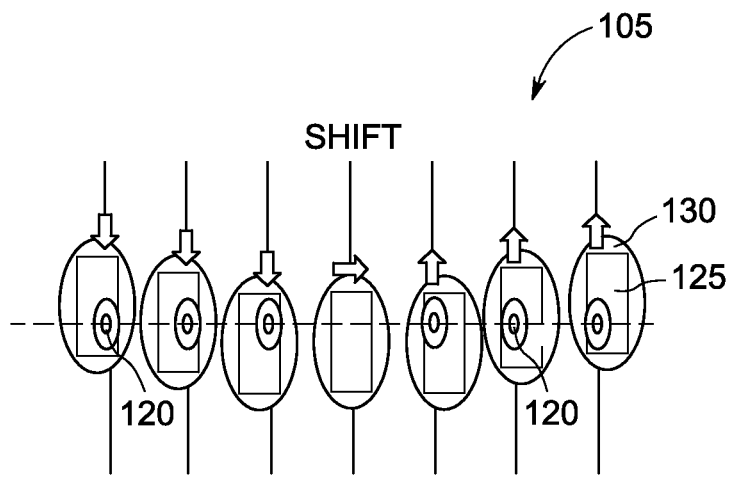
FIG. 5 is a front plan view of the anode of FIG. 2, showing vertical movement in combination with left/right movement of the focal spot position over time.

Referring to FIGS. 3-5, the position of anode 105 with respect to cathode 110 can be controlled by linear actuator 135. Spring 140 connected to anchor 145 and anode 105 assists in oscillation during operation of linear actuator 135. FIG. 4 shows an exemplary oscillatory translation of single anode 105 as viewed from cathode 110 in FIG. 2 with motion of linear actuator 135. With movement parallel to cathode 110, focal spot 120 is moved across target 125 to assist with both spreading heat and reducing the chance of melting or cracking target area 125, enabling high power output. Anode base 130 can incorporate both passive and active heat dissipation configurations as known in the art. Target 125 can be formed of tungsten, but other materials high in melting point temperature and atomic number, like molybdenum and rhodium, may also be used, depending on desired application. A control system (not shown) is coupled to the linear actuator 135 to coordinate the translation anode 105 with the generation of the stream of electrons. FIG. 5 shows a positioning diagram of focal spot 120 moved continuously up and down by linear actuator as well as left/right stepped motion to further spread out heat generated by X-ray generation at focal spot 120.

Figure 6:
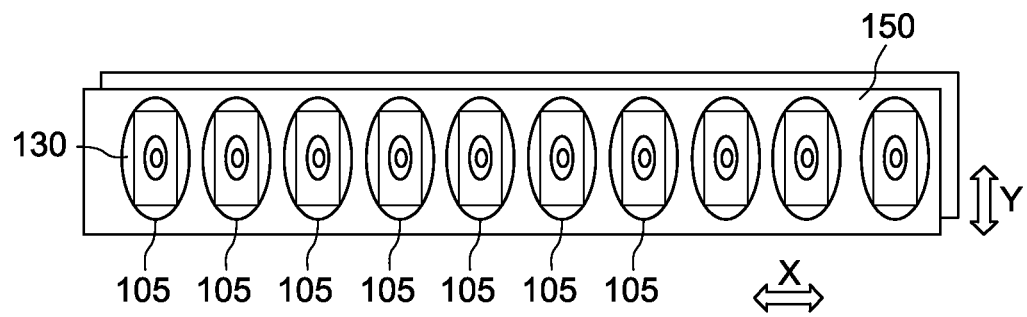
FIG. 6 is a front plan view of a plurality of anodes of FIG. 2, showing a common backplane for global movement of the anodes with respect to their respective cathodes.

Referring now to FIG. 6, in the case of distributed source X-ray configurations, multiple anodes 105 are connected to common backplane 150 to provide for global translation of all anodes 105 in either the X direction, Y direction, or a combination of both X and Y directions with respect to each respective cathode 110. Efficiency is gained by the global motion of all anodes 105 with one actuator. Alternatively, each anode 105 can be controlled by an independent respective linear actuator 135 as shown in FIG. 3 for independent translation irrespective of other anodes 105. A tomographic data acquisition is accomplished by the multi-anode configuration in FIG. 6 by energizing the sequence of cathodes 105 where each anode 105 delivers x-rays at a different imaging angle through the subject.

Figure 7A:
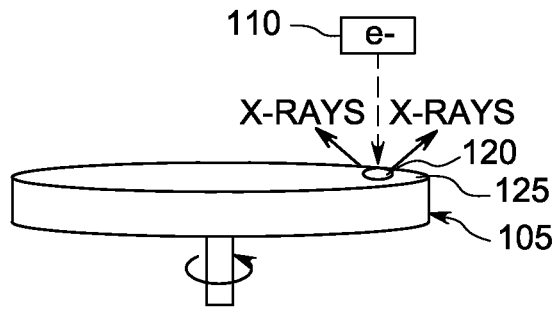
FIGS. 7A-7B are side views of anodes according to exemplary embodiments of the present disclosure, showing a flat disk anode and respective curved anode for fan-like oscillatory motion of the anode with respect to a corresponding cathode.
Figure 7B:
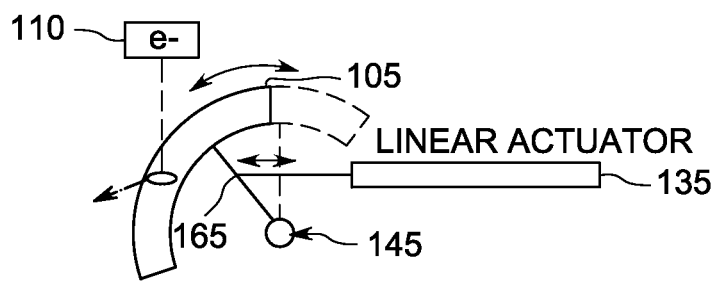

FIGS. 7A-7B show alternative embodiments of anode 105. FIG. 7A shows a substantially flat rotating disk anode 105 for heat spreading at focal spot 120 on the moving target 125. FIG. 7B shows a curved anode 105 connected to linear actuator 135. Linear actuator 135 connects to rigid brace 165 such that the motion of linear actuator 135 is converted to rotary translation of anode 105 to present a constant focal spot 120 for cathode 110. Anode 105 can either be a single anode 105, or multiple individual anodes 105.

Figure 8:
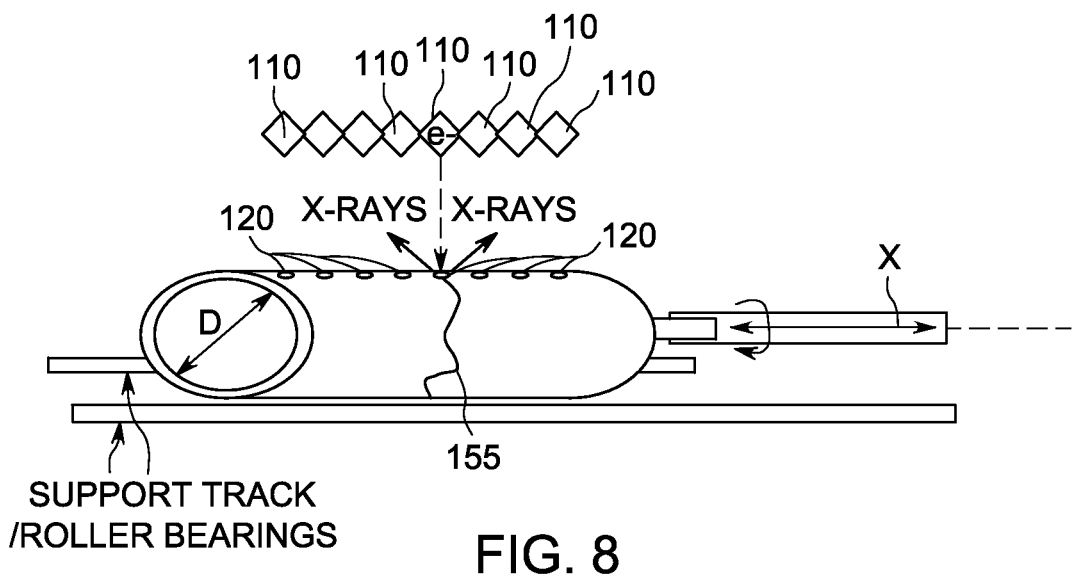
FIG. 8 is a side perspective view of an anode for an X-ray tube according to an exemplary embodiment of the present disclosure, showing a linear and rotary movement of a cylindrical anode with a plurality of stationary cathodes.

Referring now to FIG. 8, a side perspective view of a second embodiment of the X-ray tube is shown having multiple cathodes 110 and a cylindrical anode 105. In one exemplary embodiment, the translation of the cylindrical anode 105 relative to the multiple cathodes 110 can be actuated by rotation of the cylinder about its axis. Alternately, lateral motion along the axis or a combined rotation and lateral axis-parallel motion can provide mutual translation of cathode and anode.

A tomographic data acquisitions can be accomplished by this configuration when the system control energizes the multiple cathodes 110 so as to create data from multiple imaging angles through the subject. Each focal spot 120 is spread along anode 105 in an oscillating track 155 due to either rotary rotation of anode 105 or along with a combination linear motion in the X direction by linear/rotary actuator 160. Each focal spot 120 generated by a corresponding cathode 110 therefore is provided with distributed heat dissipation due to some combination oscillatory and lateral translation of anode 105. The translation of anode 105 can be in either a stepped motion or at a constant speed. Multiple speed setting can be provided in proportion to a current density of the stream of electrons generated by the cathode.

Figure 9:
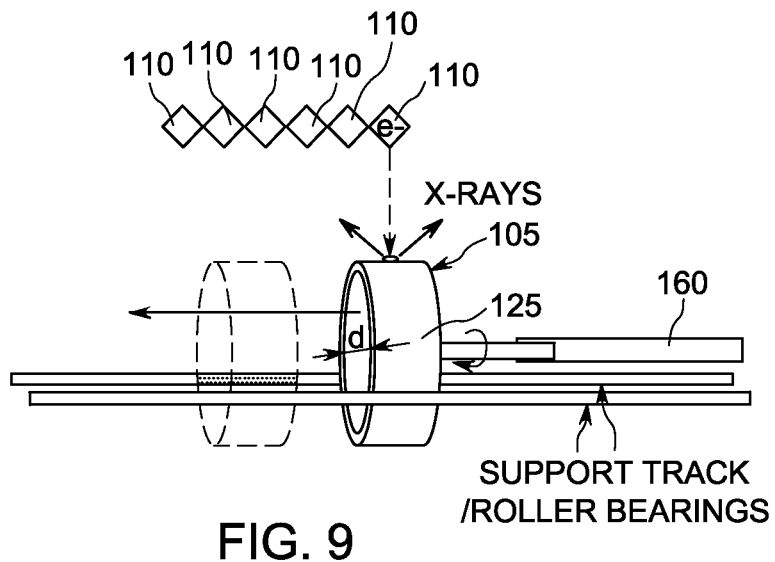
FIG. 9 is a side view of the anode of FIG. 8, showing a plurality of stationary cathodes and a single anode connected to a linear/rotary actuator.

Referring now to FIG. 9, the plurality of cathodes 110 are stationary and spread across a distance greater than the height of single anode 105. In this embodiment, anode 105 presents a single target area 125 common to all cathodes 110 and linear/rotary actuator 160 controls both the lateral position and rotation speed of anode 105. The translation of anode 105 can be in either a stepped motion or at a constant speed in proportion to a current density of the stream of electrons generated by the cathode.

Figure 10A:
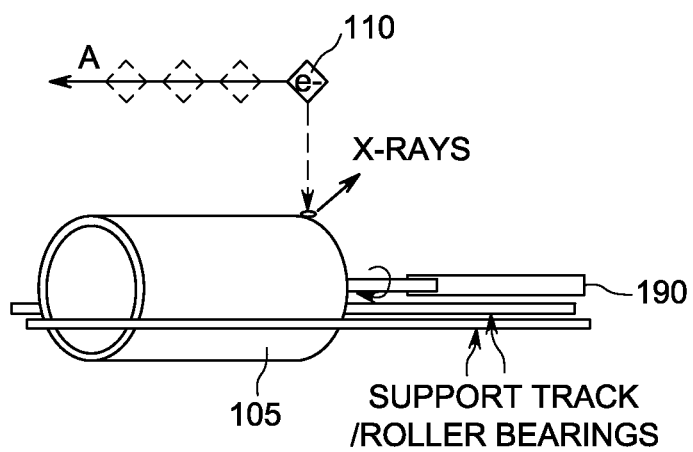
FIGS. 10A-10B are side views of an anode for an X-ray tube according to an exemplary embodiment of the present disclosure, showing a single cylindrical anode and a plurality of cylindrical anodes connected to a rotary actuator and a single movable cathode.
Figure 10B:
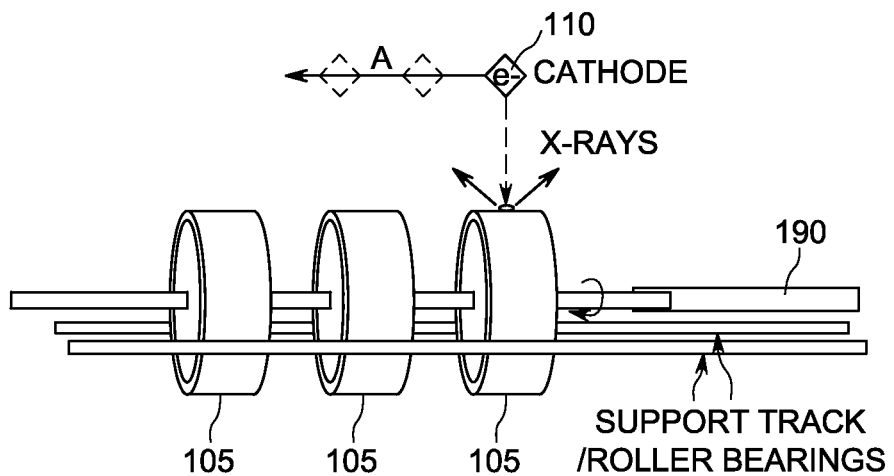

Referring now to FIGS. 10A-10B, anode 105 is configured to rotate about its longitudinal axis with no lateral movement by rotary actuator 190. Movable cathode 110 is connected to an actuator (not shown) and is configured to traverse laterally in the direction of arrow A. The lateral translation of cathode 110 can be in a stepped or continuous motion. As seen in FIG. 10B, a plurality of individual anodes 105 can be linked by common rotary actuator 190 and movable cathode 110 traverses laterally to illuminate the face of each anode 105 from a control system (not shown).

Figure 11A:
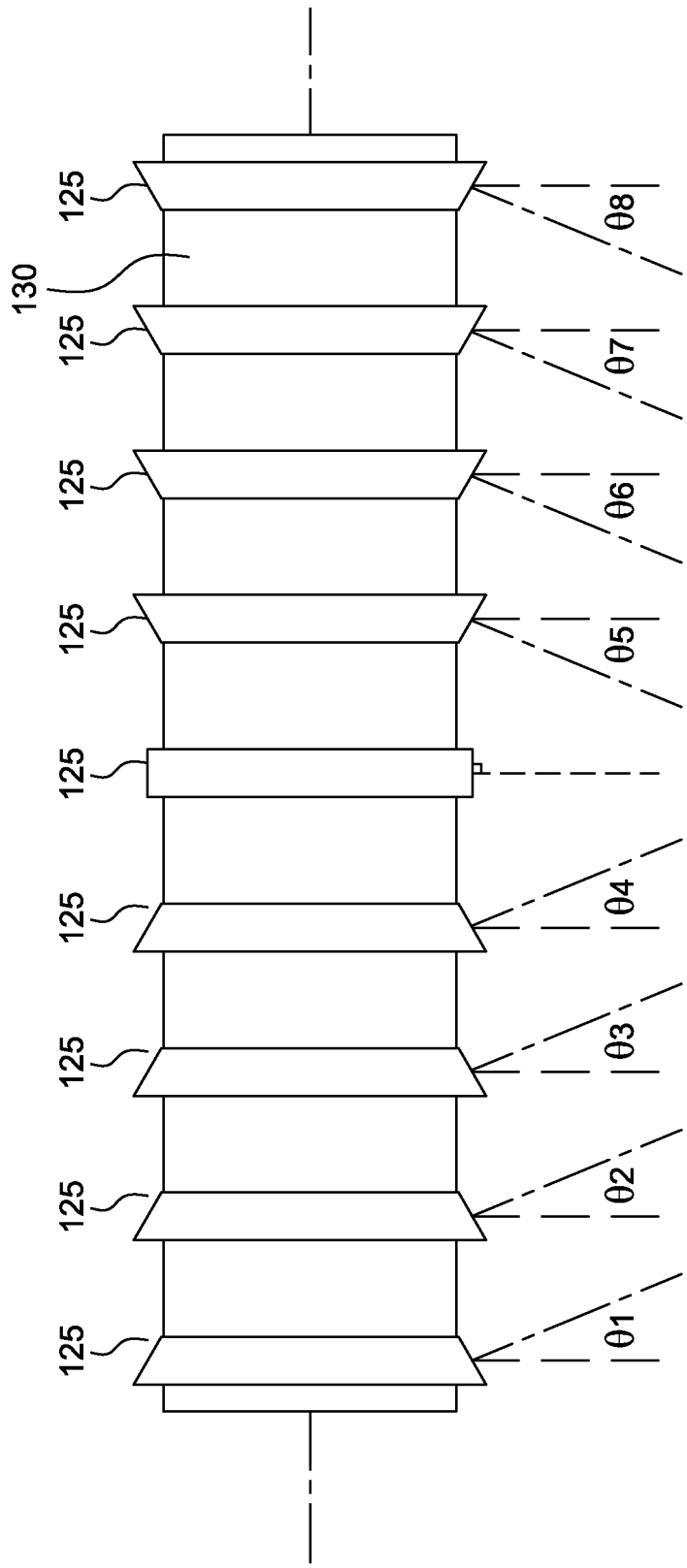
FIG. 11A is a side view of an anode for an X-ray tube according to an exemplary embodiment of the present disclosure, showing varying slope anode targets along a cylindrical anode base.
Figure 11B:
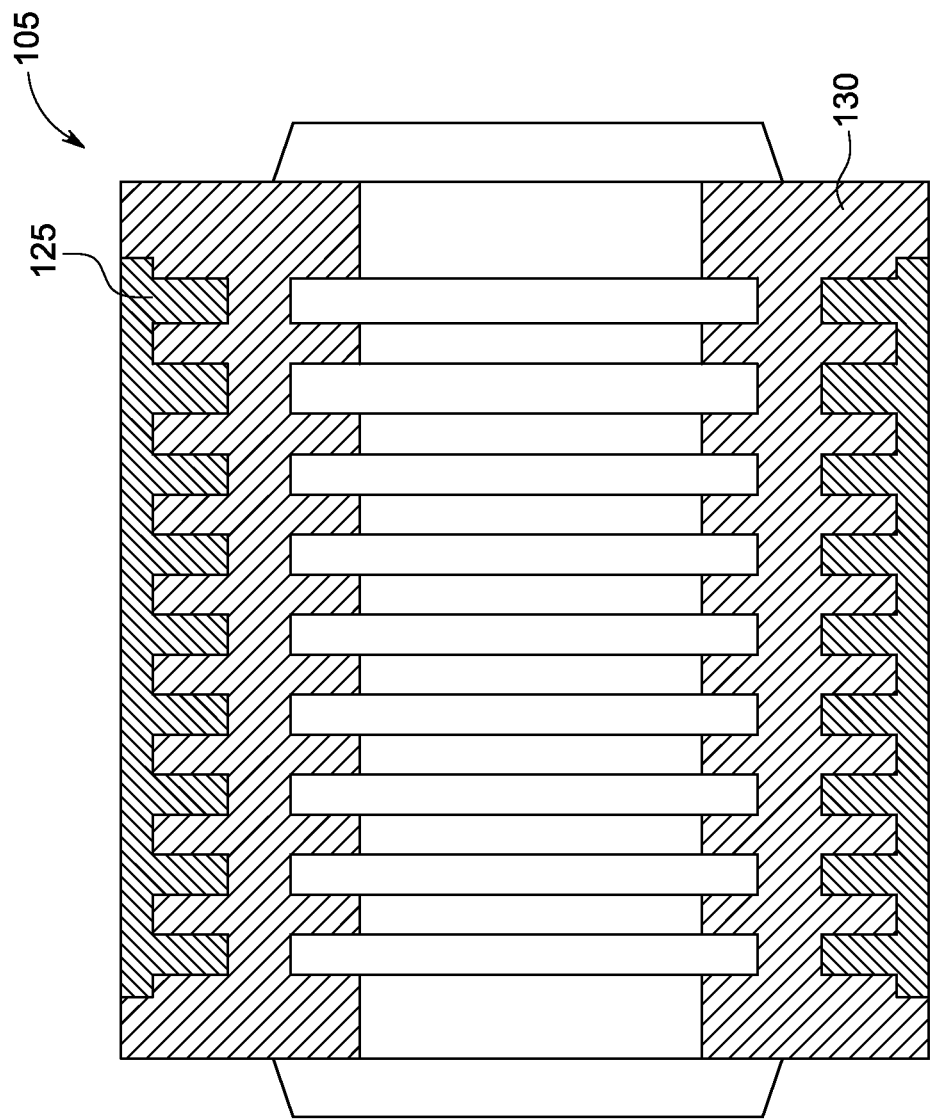
FIG. 11B is a side view of an anode for an X-ray tube according to an exemplary embodiment of the present disclosure, showing a continuous anode target formed on top of a cylindrical anode base.

FIG. 11A is a front views of an exemplary embodiment of a cylindrical anode 105 with angular anode targets 125. Angles θ1 through θ8, etc. can be predetermined to provide for angled X-ray generation due to the angular slope of each anode target 125. Predetermined collimators 115 adjacent to each focal spot location, (such as collimator 115 in FIG. 2 but not shown in FIG. 11A) further define angles θ1 through θ8. These predetermined angles provide consistent illumination area 26 on detection surface along the axis of cylindrical anode 105. This arrangement of angles presents a directional aiming of a resulting X-ray output from the anode element to the detector. FIG. 11B shows an internal construction of cylindrical anode 105 having a continuous anode target 125 coating on top of anode base 130.

Figure 12:
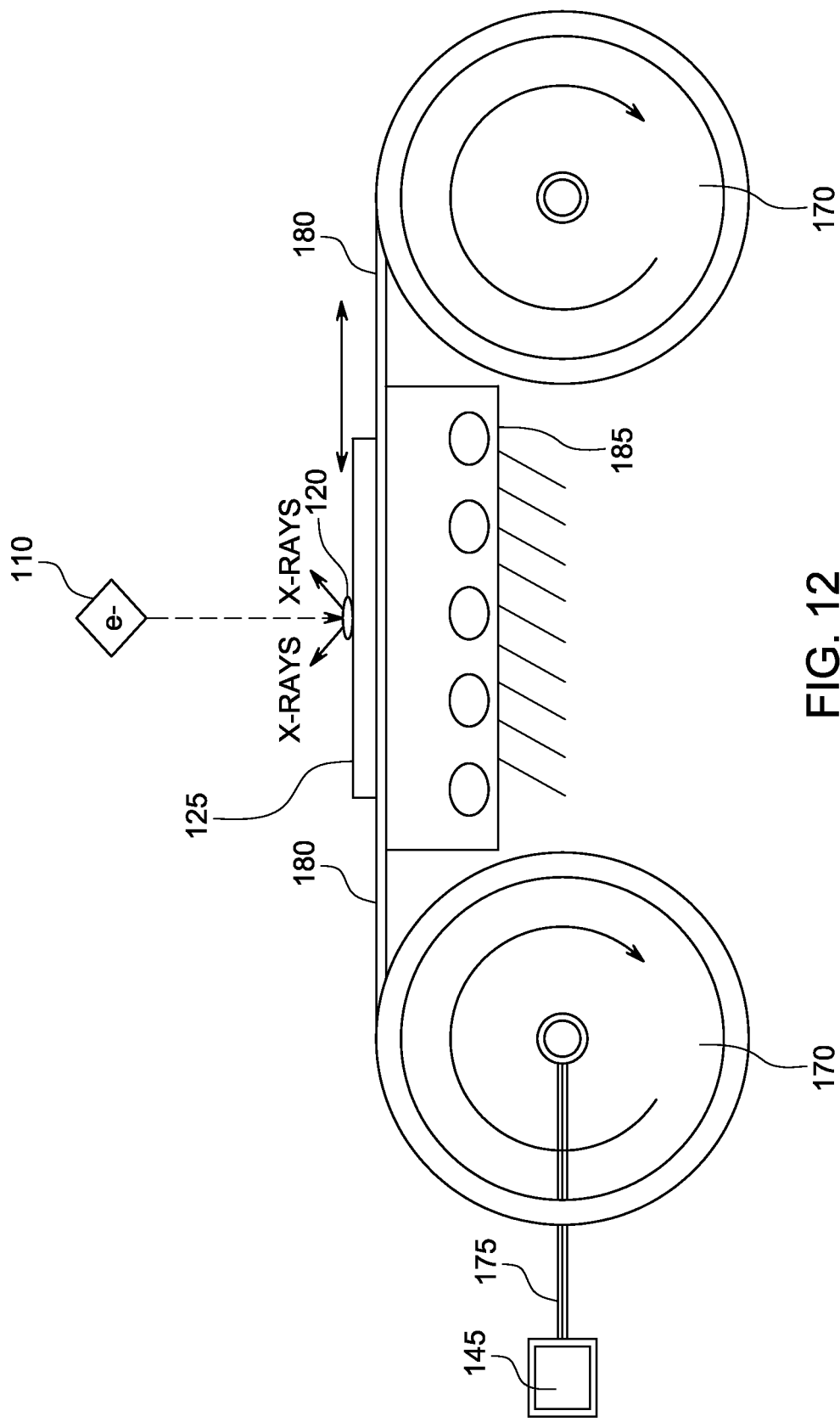
FIG. 12 is a side view of an anode for an X-ray tube according to an exemplary embodiment of the present disclosure, showing a spooled movement anode formed on a wire tape.
Figure 13:
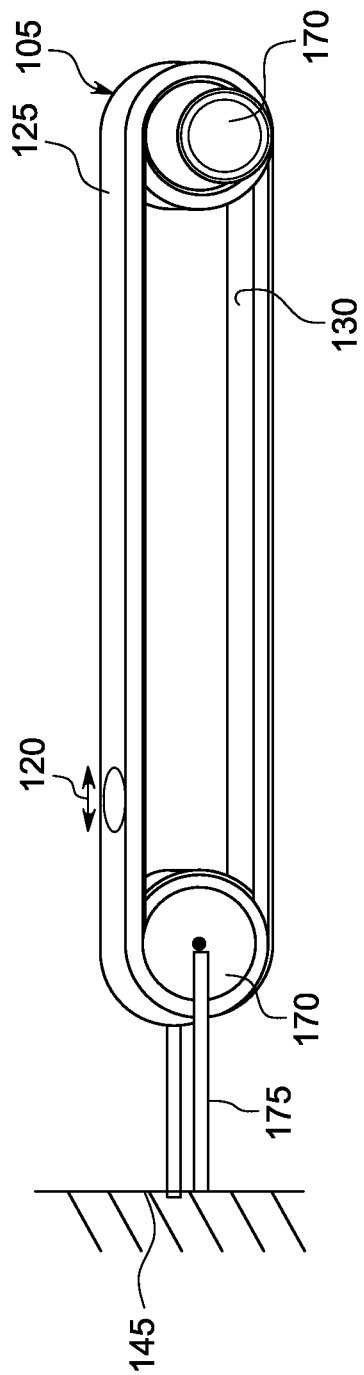
FIG. 13 is a side view of an anode for an X-ray tube according to an exemplary embodiment of the present disclosure, showing a continuous belt anode.

FIGS. 12-13 show side views of spool driven anodes 105. Referring now to FIG. 11, spools 170, which may be coupled to anchor 145 via rigid brace 175, are used to control lateral position of anode target 125 with respect to cathode 110. Heat generated by anode target 125 is dissipated by heat sink 185 located behind anode target 125. Anode target 125 presents a constant focal point 120 distance from cathode 110 by parallel movement of anode target 125 with respect to cathode 110. As can be appreciated, FIG. 11 is configured for oscillatory lateral movement as compared to FIG. 12. FIG. 12 shows a belt shaped anode base 130 coated with a continuous anode target 125.

The invention claimed is:

1. An X-ray source comprising:
    a cathode element adapted to generate a stream of electrons;
    an anode element adapted to present a focal spot position for the stream of electrons;
    a vacuum chamber containing the cathode element and anode element;
    at least one actuator configured to translate at least one of the anode element or the cathode element with respect to each other, wherein at least one of the at least one actuators is a linear actuator;
    a spring coupling the anode element to an anchor to facilitate a linear oscillatory motion of the anode element; and a control system coupled to the at least one actuator and adapted to coordinate the translation of at least one of the anode or the cathode with the generation of the stream of electrons.

2. The X-ray source of claim 1, wherein the anode element is cylindrically shaped.

3. The X-ray source of claim 1, wherein the at least one actuator is configured to rotate the anode element with respect to the cathode element; and
wherein the control system is adapted to coordinate the rotation of the anode with the generation of the stream of electrons.

4. The X-ray source of claim 1, wherein the at least one actuator configured to translate the anode element with respect to the cathode element is further configured to rotate the anode element with respect to the cathode element.

5. The X-ray source of claim 1, wherein the at least one actuator is adapted to translate the anode element in a stepped manner with respect to the cathode element.

6. The X-ray source of claim 1, wherein the control system is configured to translate the anode element at a constant speed in proportion to a current density of the stream of electrons generated by the cathode.

7. The X-ray source of claim 1, further comprising:
a heat sink operatively coupled to the anode element.

8. The X-ray source of claim 1, wherein the control system is operatively coupled to a cathode power source, the control system configured to implement a sequence of a plurality of electron generation periods through control of the cathode power source for different translated positions along the anode element.

9. An X-ray source, comprising:
a plurality of cathode elements each adapted to generate a stream of electrons;
a cylindrically shaped anode element adapted to present a focal spot position for each of the stream of electrons, wherein the focal spot position is disposed on an outer lateral surface of the cylindrically shaped anode element;
a vacuum chamber containing the plurality of cathode elements and the anode element;
at least one actuator configured to translate at least one of the anode element or the plurality of cathode elements with respect to each other; and
a control system coupled to the at least one actuator and adapted to coordinate the translation of at least one of the anode or cathode with the generation of each stream of electrons.

10. The X-ray source of claim 9, wherein the at least one actuator is configured to rotate the anode element with respect to the plurality of cathode elements; and
wherein the control system is adapted to coordinate the rotation of the anode with the generation of each stream of electrons.

11. The X-ray source of claim 9, wherein the at least one actuator configured to translate the anode element with respect to the cathode element is further configured to rotate the anode element with respect to each of the plurality of cathode elements.

12. The X-ray source of claim 9, further comprising:
a heat sink operatively coupled to the anode element.

13. The X-ray source of claim 9, wherein the at least one actuator is adapted to translate the anode element in a stepped manner with respect to the cathode element.

14. The X-ray source of claim 9, wherein the control system is configured to translate the anode element at a constant speed in proportion to the current density of the stream of electrons generated by the cathode.

15. The X-ray source of claim 9, further comprising:
a plurality of spools; and
a flexible substrate operatively coupled to the plurality of spools, the flexible substrate being coupled to the anode element and configured and adapted to facilitate linear movement of the anode element.

16. The X-ray source of claim 9, wherein the control system is operatively coupled to a cathode power source, the control system configured to implement a sequence of a plurality of electron generation periods through control of the cathode power source at different translated positions along the anode element.

* * * * *